(12) United States Patent
Minkoff et al.

(10) Patent No.: US 6,437,569 B1
(45) Date of Patent: Aug. 20, 2002

(54) EXPANDABLE MRI RECEIVING COIL

(75) Inventors: Lawrence A. Minkoff, Lattingtown; Valentin Fuster, New York, both of NY (US); Meir Shinnar, Teaneck, NJ (US); Zahi A. Fayad, New York; Juan J. Badimon, Larchmont, both of NY (US)

(73) Assignees: Magna-Lab Inc, Syosset; Mount Sinai School of Medicine of the City University of New York, New York, both of NY (US)

( * ) Notice: Subject to any disclaimer, the term of this patent is extended or adjusted under 35 U.S.C. 154(b) by 0 days.

(21) Appl. No.: 09/888,613

(22) Filed: Jun. 25, 2001

Related U.S. Application Data

(63) Continuation of application No. 09/442,666, filed on Nov. 18, 1999, now abandoned.
(60) Provisional application No. 60/108,968, filed on Nov. 18, 1998.

(51) Int. Cl.⁷ .................................................. G01V 3/00
(52) U.S. Cl. ........................ 324/318; 600/422; 600/423
(58) Field of Search ................................ 324/318, 321, 324/322, 300, 306, 307, 309, 311, 314; 600/407, 421, 423, 422, 410

(56) References Cited

U.S. PATENT DOCUMENTS

| 5,413,104 | A | * | 5/1995 | Buijs et al. | 600/423 |
| 5,451,232 | A | * | 9/1995 | Rhinehart et al. | 606/192 |
| 5,476,095 | A | * | 12/1995 | Schnall et al. | 600/423 |
| 5,928,145 | A | * | 7/1999 | Ocali et al. | 324/307 |
| 6,051,974 | A | * | 4/2000 | Reisker et al. | 324/318 |

* cited by examiner

Primary Examiner—Louis Arana
(74) Attorney, Agent, or Firm—Darby & Darby

(57) ABSTRACT

A magnetic resonance image receiving coil includes a first balloon having a longitudinal axis. An internal surface of the first balloon defines an internal inflatable chamber. A second balloon has a longitudinal axis. The second balloon is disposed about the first balloon. A plurality of longitudinally extending grooves are disposed in one of an external surface of the first balloon and the internal surface of the second balloon. A first wire is disposed in at least one of the grooves. A second wire is disposed in at least a second one of the grooves. Each of the first wire and the second wire is adapted to be electrically connected to an MRI apparatus. In accordance with an alternate embodiment, the first and second wires are disposed in grooves in a sheath which is disposed between the first and second balloons. In accordance with a further alternate embodiment, the first and second wires are disposed in guide tubes that are connected to the external surface of a balloon.

33 Claims, 4 Drawing Sheets

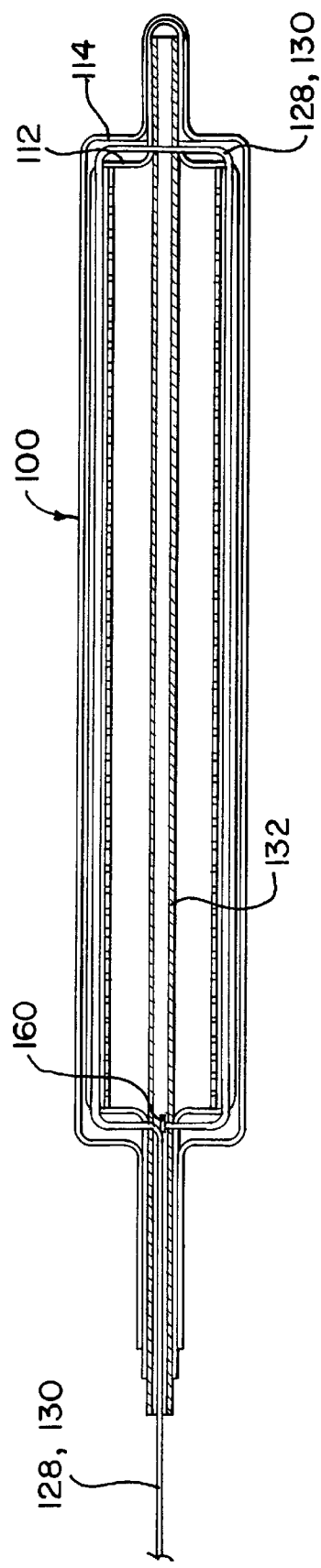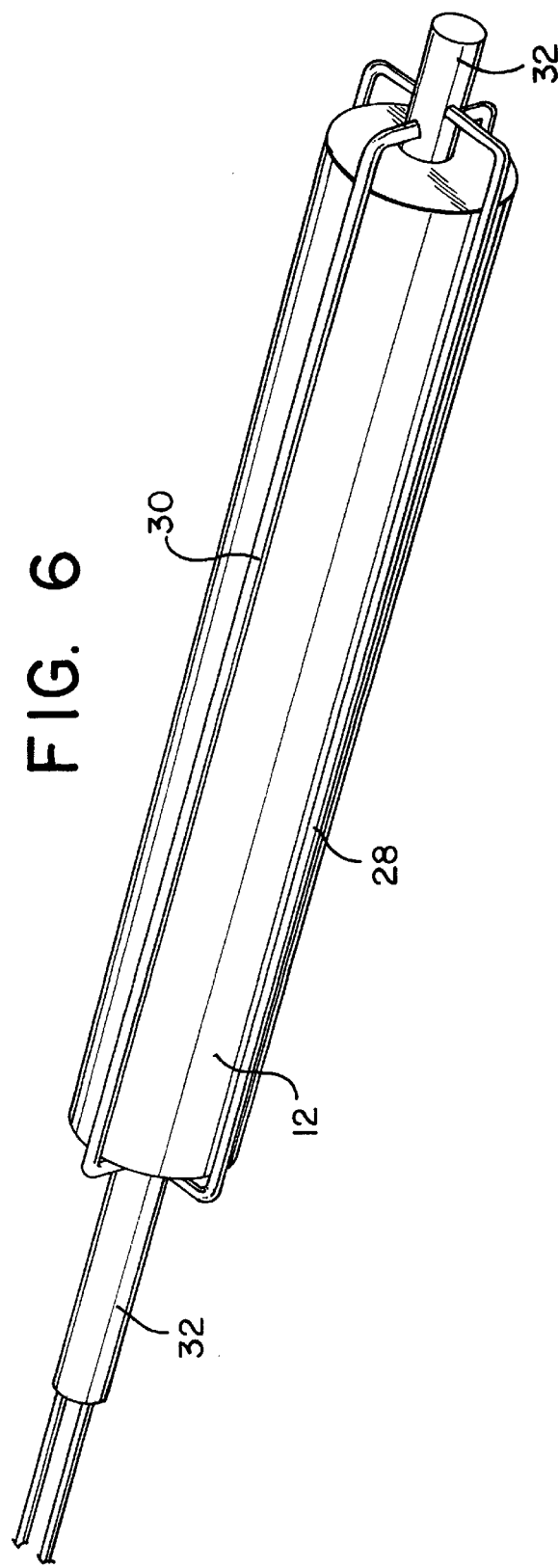

EXPANDABLE MRI RECEIVING COIL

This is a continuation of application Ser. No. 09/442,666, filed Nov. 18, 1999, now abandoned; which claims priority from Provisional Application Serial No.: 60/108,968, filed Nov. 18, 1998, which is now expired. Each of these prior applications is hereby incorporated herein by reference, in its entirety.

BACKGROUND OF THE INVENTION

1. Field of the Invention

The present invention relates to an expandable MRI receiving coil. More specifically, the present invention relates to an expandable internal MRI receiving coil that has a first wire loop and a second wire loop, such that the plane of the first wire loop is positioned 90° from the plane of the second wire loop to produce a signal that is 90° out of phase with respect to the signal produced by the second wire loop.

2. Discussion of the Related Art

Currently there are over 1.2 million angiography procedures performed annually in the United States. These procedures are performed to provide images of the cardiac system to physicians. But traditional X-ray angiography will only provide a physician with information regarding blood flow, and the amount of an occlusion in the vessel. Moreover, the reasons for an occlusion may not be apparent because no information regarding the underlying biochemistry of the occlusion is provided by these conventional techniques.

Magnetic resonance imaging is based on the chemistry of the observed tissue. Therefore, MRI provides not only more detailed information of the structures being imaged, but also provides information on the chemistry of the imaged structures. For example, most heart attacks occur in vessels that are less than 50% occluded with plaque. But there are different types of plaque. One type of plaque is very stable and is not likely to cause problems. However, another type of plaque is unstable, if it becomes pitted or rough it is possible for blood to clot and occlude the vessel. These different types of plaque that are contained within the blood vessels can be identified by MRI as has been described, for example, by J. F. Toussaint et al., Circulation, Vol. 94, pp. 932–938 (1996). Conventionally, MR imaging of the heart has been achieved with the use of a body coil (i.e., a receiving coil that completely surrounds the torso) and specialized surface coils designed for cardiac use. However, an external body coil provides a relatively low signal to noise (SNR) when the object to be imaged is small and distant from the coil as is the heart (especially the rear portion thereof) and the aorta. Surface coils do increase the SNR in those regions close to the coil, but not to those at any distance from the coil.

Thus, in producing an MR image, it is desirable to increase the SNR as much as possible. As a general rule, the closer the receiving coil is to the object to be imaged, the better the SNR will be. Thus, to produce an image of the heart and/or the aorta, it is preferable to place a receiving coil within the body (i.e., an internal receiving coil). Additionally, for internal receiving coils, the larger the diameter of the receiving coil, the larger its area will be thereby improving its SNR.

SUMMARY OF THE INVENTION

It is an object of the present invention to obtain an MR image of an object deep within the body having a relatively high SNR. This is accomplished by using a receiving coil that can be passed through the esophagus into a position adjacent to the heart and its surrounding vessels so that an MR image of the heart, the aortic arch and the other major vessels of the heart can be made. The receiving coil has a pair of loops that are oriented 90° relative to each other so that their respective signals are 90° out of phase and the resultant combined image from these signals will be more symmetrical.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 5 is a cross-sectional view of the MRI probe showing only one coil, its tuning capacitor, central shaft, and the internal and external balloons;

FIG. 6 is a perspective view of the internal balloon and the wire loops in quadrature.

DETAILED DESCRIPTION OF THE PREFERRED EMBODIMENT

Figure 1:
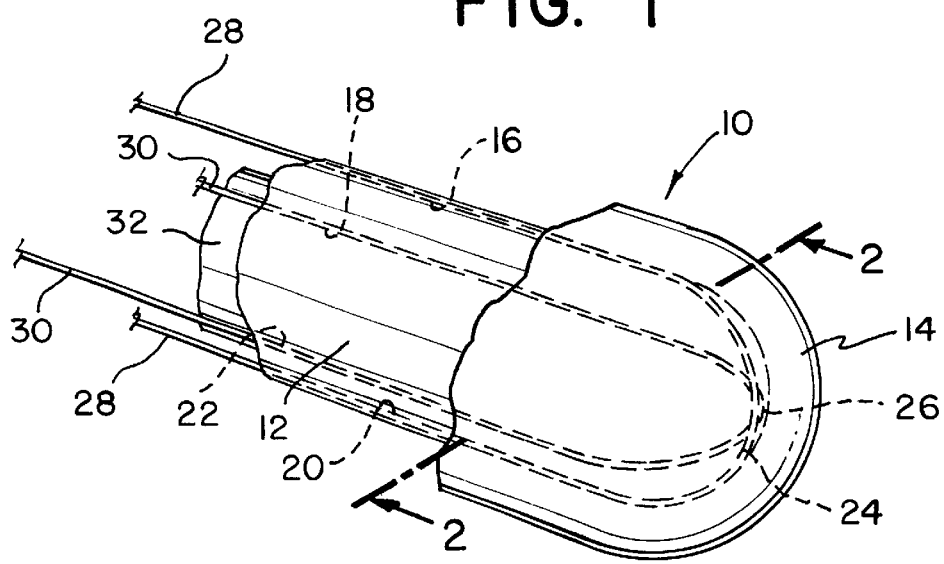
FIG. 1 is a partial perspective view of an expandable MRI balloon receiving coil in accordance with the present invention.

Referring now to FIG. 1, a partial perspective view of an MRI probe 10 is illustrated. Probe 10 includes an inner balloon 12 and an outer balloon 14.

Figure 2A:
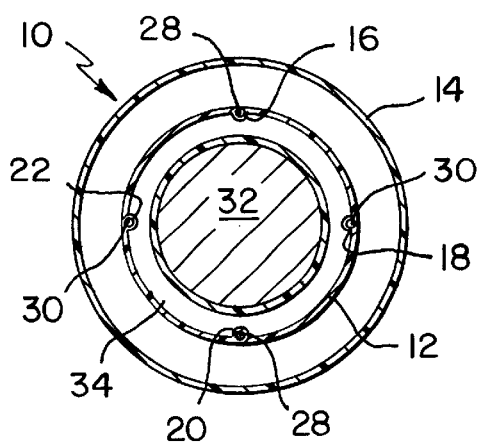
FIG. 2A is a cross-sectional view of one embodiment of the present invention, taken along line 2—2 of FIG. 1 and looking in the direction of the arrows.

In a first embodiment, which is illustrated in FIG. 2A, balloon 12 has four axially extending grooves 16, 18, 20 and 22 in its outer surface. Groove 16 is disposed generally diametrically opposite from groove 20. Likewise, groove 18 is disposed generally diametrically opposite from groove 22. Thus, adjacent grooves are disposed at 90° intervals. At the distal end 24 of inner balloon 12, grooves 16, 18, 20, 22 curve radially inwardly and intersect at the distal tip or apex 26 of inner balloon 12. Thus, as viewed from the front, grooves 16, 18, 20 and 22 appear to intersect at 90° angles, thereby resembling cross hairs. A first wire 28 is placed within grooves 16, 20. A second wire 30 is placed within grooves 18, 22. Wires 28, 30 are insulated from one another at least at their point of intersection at distal tip 26. Wires 28, 30 are fixedly held within grooves 16, 20, 18 and 22. In a currently preferred embodiment, wires 28, 30 are glued within their respective grooves 16, 20 and 18, 22, respectively.

A shaft 32 is disposed within inner balloon 12. If shaft 32 is used, it is preferably a plastic tube of appropriate size and is formed from an elastic material that has sufficient flexibility to allow probe 10 to enter the human body through either the mouth or nose and, thereafter, be placed within the esophagus. Shaft 32 preferably has an outer diameter of less than 3/16" if it is to enter into the mouth and less than 1/4" if is to be inserted into the nose. An annular space 34 is disposed between shaft 32 and inner balloon 12. Annular space 34 is, at its proximal end, fluidly connected to a conduit (not shown), which is connected to a source of fluid pressure to selectively inflate and deflate the inner balloon as desired. Additionally, as those skilled in the art will readily recognize, wires 28, 30 form two loops that are electrically connected at their proximal end via interface circuits for impendence matching (not shown). The interface circuits are then electrically connected to a conventional MRI apparatus (e.g., an MRI spectrometer) to produce an image based upon a signal received by wires 28, 30.

Figure 3:
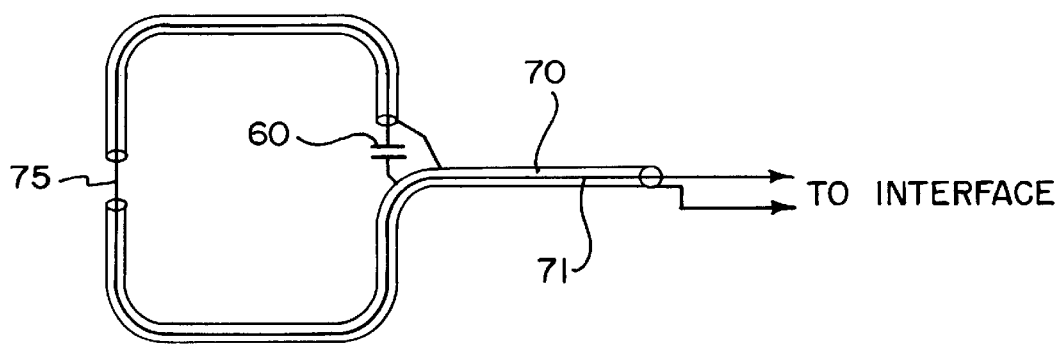
FIG. 3 is a schematic illustration of the wires in the form of two loops of coaxial cable connected in series with a tuning capacitor.
Figure 4:
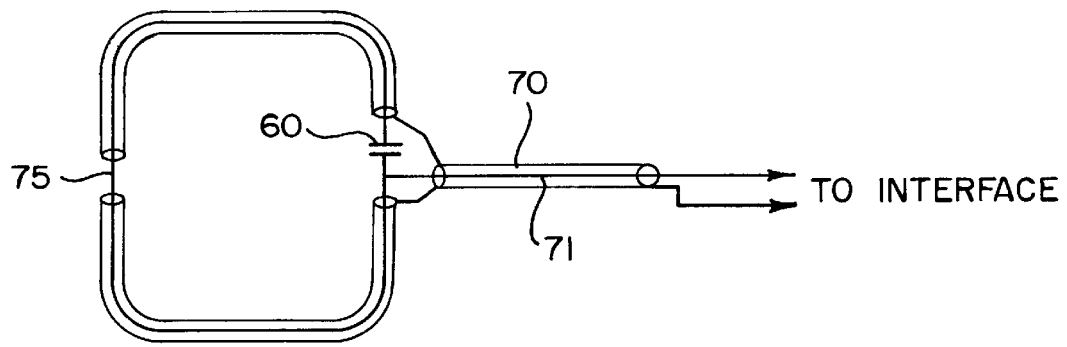
FIG. 4 is a schematic illustration of the wires in the form of two loops of coaxial cable connected in parallel with a tuning capacitor.

Wires loops 28, 30 are preferably each formed from coaxial cable that may be connected to a tuning capacitor 60 either as shown in FIG. 3 in a series circuit or as shown in FIG. 4 in a parallel circuit. In the currently preferred embodiment, the parallel circuit is used because it provides at least twice the SNR of a series circuit. In any of the below embodiments, wire loops 28, 30 are each preferably formed from coaxial cable, which has an outer conductor 70 and an inner conductor 71. For both wire loops 28, 30, the approximate midpoints of the outer conductor 70 has a gap 75. While gap 75 is provided at or near the point of intersection of wires 28,30, the wires are still insulated from one another. Wires 28,30 are disposed at approximately 90° intervals. Thus, the signal produced by wire 28 and 30 are said to be in quadrature. Therefore, the resulting image produced from the signals received from wires 28, 30 is more symmetrical than a conventional receiving coil. The MRI apparatus can be, for example, a GE Signa, 1.5 Tesla, which is commercially available from General Electric Company.

In operation, the probe 10 is initially in a deflated state and the outer surface of outer balloon 14 is preferably well lubricated with a conventional, sterile, water-soluable lubricant. The distal end 24 of the probe is then inserted into the body through either the mouth or the nose. Distal end 24 is further inserted into the body until it passes into the esophagus. The receiving coil is placed in the desired position within the esophagus, as close to the object to be imaged as possible. For example, for the closest approach to the heart and the aortic arch, the receiver coil should be placed within the esophagus behind and under the heart and the aortic arch. The balloon assembly is inflated to maintain the position of the receiver coil within the esophagus and so that the receiver coil will be as large in diameter as possible without causing harm to the esophagus. Of course, the amount that the balloon is inflated will vary from patient to patient, but will typically will be on the order of about 1/2 inch in diameter by 5 inches in length when inflated.

The receiving coil alone may be sufficient to obtain an adequate image of the aortic arch. Alternatively, an external surface MRI receiving coil may be placed on the patient to produce a combined image from the internal probe 10 and the external receiving coil (not shown). A method of generating a combined image of the heart and the vessels emanating from the heart, from the combination of a first image from a coil placed within the body and a second image from a coil placed externally to the body is disclosed in Applicants' copending application Ser. No. 09/081,908, entitled "Cardiac MRI With An Internal Receiving Coil and An External Receiving Coil", filed on May 20, 1998, the disclosure of which is hereby fully incorporated by reference.

Figure 2B:
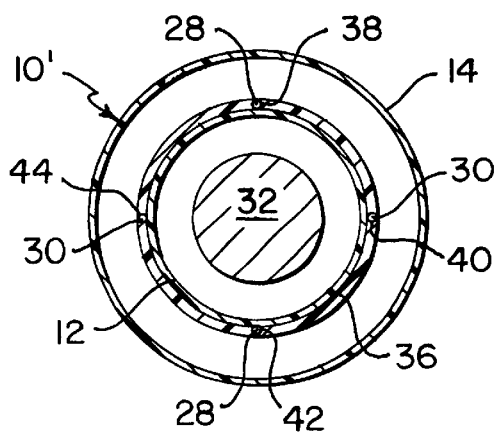
FIG. 2B is a cross-sectional view of another embodiment of the present invention, taken along line 2—2 of FIG. 1 and looking in the direction of the arrows.

Referring now to FIG. 2B, an alternate embodiment of probe 10' is illustrated. In this embodiment, an intermediate tubular sheath 36 is disposed between inner balloon 12 and outer balloon 14. Sheath 36 is formed with grooves 38, 40, 42, 44 to receive wires 28, 30. Sheath 36 is made from an elastic material, such as, for example, latex, to permit tubular sheath 36 to expand when inner balloon 14 is inflated once the probe has been placed in the esophagus.

Figure 2C:
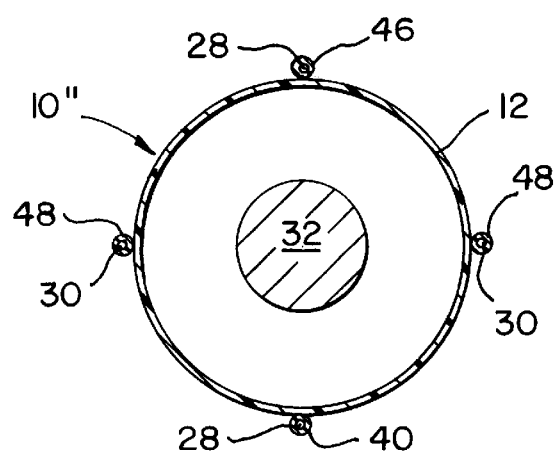
FIG. 2C is a cross-sectional view of yet another embodiment of the present invention, taken along line 2—2 of FIG. 1 and looking in the direction of the arrows.

Referring now to FIG. 2C, a further alternate embodiment of probe 10" is illustrated. In this embodiment, a plurality of guide tubes 46, 48 are placed on the exterior surface of balloon 12. Each guide tube extends about the closed distal end 24 of balloon 12. Thus, each guide tube has a first portion that is disposed on one external side of balloon 12 and a second portion that is disposed on a generally diametrically opposite external side of balloon 12. Wire 28 is inserted into guide tube 46. Similarly, wire 30 is placed within guide tube 48. Thus, when probe 10" is placed within the esophagus, balloon 12 may be inflated to maintain the position of wires 28, 30, which together form the receiving coil within the esophagus so that the receiver coil will have as large a diameter as possible without causing harm to the esophagus.

Figure 2D:
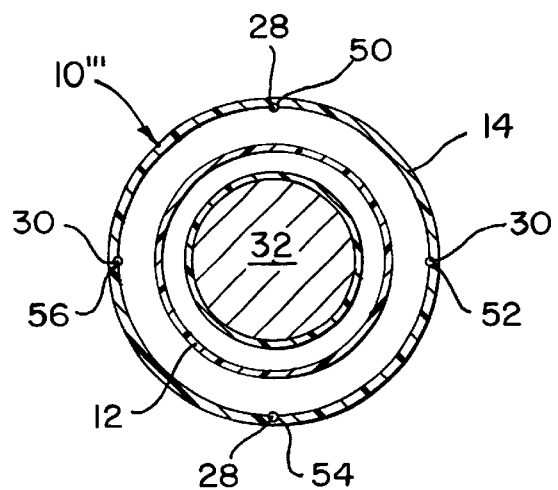
FIG. 2D is a cross-sectional view of another embodiment of the present invention, taken along line 2—2 of FIG. 1 and looking in the direction of the arrows.

Referring now to FIG. 2D, a further alternative embodiment of probe 10''' is illustrated. Grooves 50, 52, 54 and 56 are disposed within the inner cylindrical surface of outer balloon 14. Wire 28 is placed within grooves 50, 54. Similarly, wire 30 is placed within grooves 52, 56. In use, probe 10''' operates in a manner similar to the embodiments illustrated in FIGS. 2A, 2B and 2C. In other words, once the probe has been placed within the esophagus, the annular space between shaft 32 and inner balloon 12 is inflated thereby causing the entire probe to stably maintain the position of the receiving coil within the esophagus so that the receiving coil has as large a diameter as possible without causing harm to the esophagus. The receiving coil may then be used to obtain an image of, for example, the heart and/or the aortic arch.

Referring now to FIG. 5, a cross-sectional view of the MRI probe 100 is illustrated. Here a single wire loop 128 or 130 (referred to as 128, 130 in FIG. 5) is illustrated inflated on inner balloon 112. Both the wire loop and the inner balloon are covered by the outer balloon 114. Both the inner and outer balloons are subsequently attached at both ends to the central tubular shaft 132. Wire loop 128 or 130 also penetrates into the central tube 132 at both ends. At the proximal end, where the loop 128 or 130 penetrates into the central tube 132, the wire 128 or 130 continues down through central shaft 132 and out of its proximal end to the MRI spectrometer.

Figure 7:
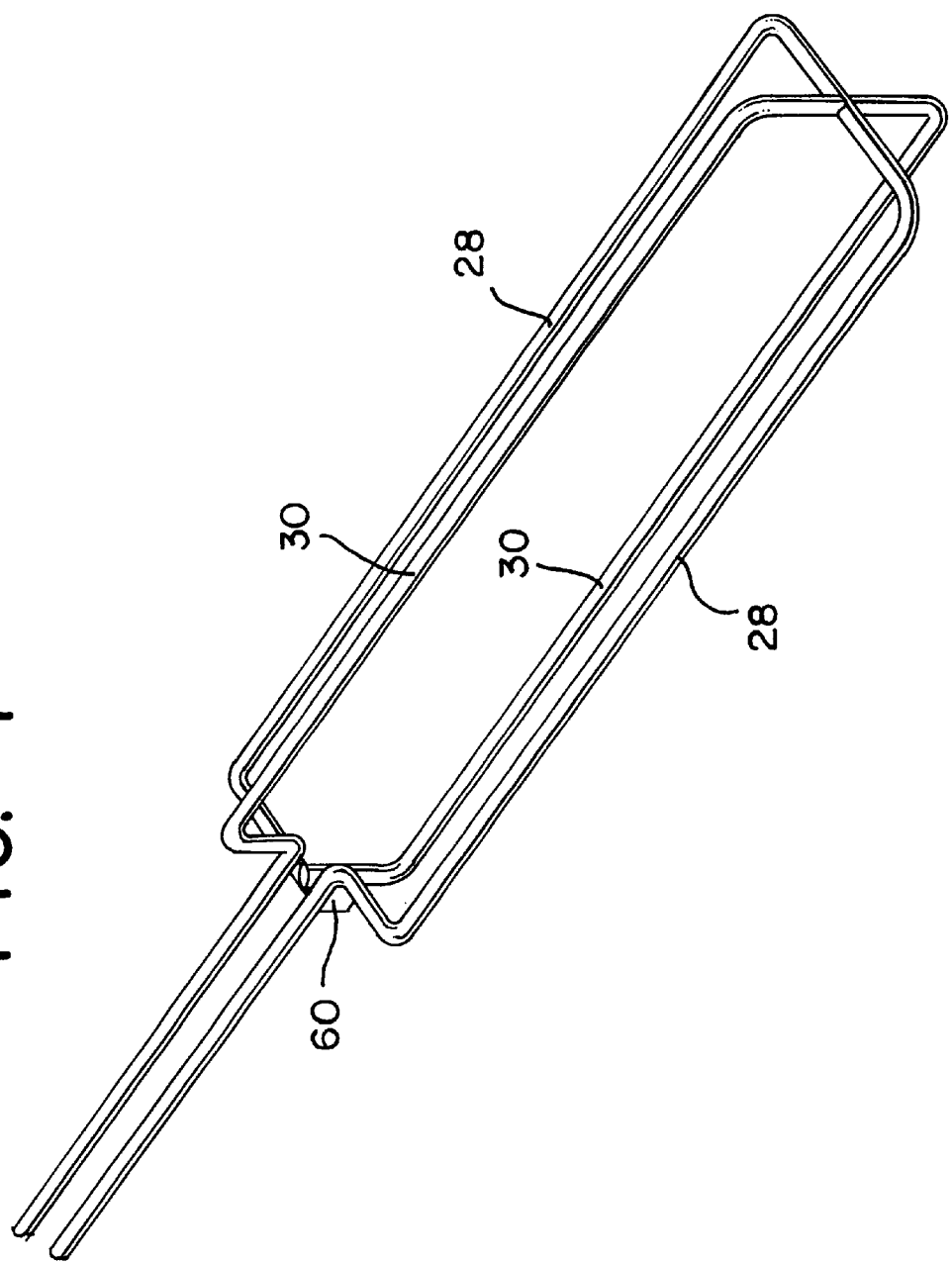
FIG. 7 is a view of two wire loops shown in quadrature, without the central shaft, internal and external balloon.

Referring now to FIG. 6, a perspective view of the wire loops 28, 30 and inflated inner balloon 12 is illustrated. Wire loops 28, 30 are shown in quadrature, with outer balloon 14 being removed for the sake of clarity on the drawings. Referring now to FIG. 7, only the wire loops 28, 30 are shown for the sake of clarity. Wire loops 28, 30 are shown in quadrature.

Having described the presently preferred exemplary embodiment of an expandable MRI receiving coil in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims.

What is claimed is:

1. A magnetic resonance image receiving coil comprising:
   a first balloon having a longitudinal axis, an internal surface of said first balloon defining an internal inflatable chamber;
   a second balloon having a longitudinal axis, said second balloon being disposed about said first balloon;
   a plurality of longitudinally extending grooves, said grooves being disposed in one of an external surface of said first balloon and an internal surface of said second balloon;
   a first wire disposed in at least one of said grooves; and
   a second wire disposed in at least a second one of said grooves, each of said first wire and said second wire having means for being electrically connected to an MRI apparatus.

2. The magnetic resonance image receiving coil in accordance with claim 1, wherein said plurality of grooves include four grooves that are disposed at approximately 90° intervals so that a first pair of said grooves are disposed generally diametrically opposite one another and a second pair of said grooves are disposed generally diametrically opposite one another.

3. The magnetic resonance image receiving coil in accordance with claim 2, wherein said first wire is disposed in said first pair of said grooves.

4. The magnetic resonance image receiving coil in accordance with claim 3, wherein said second wire is disposed in said second pair of said grooves.

5. The magnetic resonance image receiving coil in accordance with claim 4, wherein said wires are fixedly connected to said grooves.

6. The magnetic resonance image receiving coil in accordance with claim 5, wherein said wires are glued within said grooves.

7. The magnetic resonance image receiving coil in accordance with claim 5, wherein said grooves are disposed in said external surface of said first balloon.

8. The magnetic resonance image receiving coil in accordance with claim 5, wherein said grooves are disposed in said internal surface of said second balloon.

9. The magnetic resonance image receiving coil in accordance with claim 7, wherein an elastic shaft is disposed within said first balloon.

10. The magnetic resonance image receiving coil in accordance with claim 8, wherein an elastic shaft is disposed within said first balloon.

11. The magnetic resonance image receiving coil in accordance with claim 1, wherein said first and second wires are coaxial cable.

12. The magnetic resonance image receiving coil in accordance with claim 11, wherein each of said first and second wires are connected to a tuning capacitor in a parallel circuit.

13. The magnetic resonance image receiving coil in accordance with claim 11, wherein each of said first and second wires are connected to a tuning capacitor in a parallel circuit.

14. A magnetic resonance image receiving coil comprising:
   a first balloon having a longitudinal axis, an internal surface of said first balloon defining an internal inflatable chamber;
   a second balloon having a longitudinal axis, said second balloon being disposed about said first balloon;
   a sheath being disposed between said first balloon and said second balloon, said sheath having an internal surface and an external surface;
   a plurality of longitudinally extending grooves, said grooves being disposed in one of said internal surface and said external surface of said sheath;
   a first wire disposed in at least one of said grooves; and
   a second wire disposed in at least a second one of said grooves, each of said first wire and said second wire having means for being electrically connected to an MRI apparatus.

15. The magnetic resonance image receiving coil in accordance with claim 14, wherein said plurality of grooves include four grooves that are disposed at approximately 90° intervals so that a first pair of said grooves are disposed generally diametrically opposite one another and a second pair of said grooves are disposed generally diametrically opposite one another.

16. The magnetic resonance image receiving coil in accordance with claim 15, wherein said first wire is disposed in said first pair of said grooves.

17. The magnetic resonance image receiving coil in accordance with claim 16, wherein said second wire is disposed in said second pair of said grooves.

18. The magnetic resonance image receiving coil in accordance with claim 19, wherein said wires are fixedly connected to said grooves.

19. The magnetic resonance image receiving coil in accordance with claim 18, wherein said wires are glued within said grooves.

20. The magnetic resonance image receiving coil in accordance with claim 18, wherein said grooves are disposed in said external surface of said sheath.

21. The magnetic resonance image receiving coil in accordance with claim 18, wherein said grooves are disposed in said internal surface of said sheath.

22. The magnetic resonance image receiving coil in accordance with claim 20, wherein an elastic shaft is disposed within said sheath.

23. The magnetic resonance image receiving coil in accordance with claim 21, wherein an elastic shaft is disposed within said first balloon.

24. The magnetic resonance image receiving coil in accordance with claim 14, wherein said first and second wires are coaxial cable.

25. The magnetic resonance image receiving coil in accordance with claim 24, wherein each of said first and second wires are connected to a tuning capacitor in a parallel circuit.

26. The magnetic resonance image receiving coil in accordance with claim 24, wherein each of said first and second wires are connected to a tuning capacitor in a parallel circuit.

27. A magnetic resonance image receiving coil comprising:
   a first balloon having an internal surface, an external surface and a longitudinal axis, said internal surface of said first balloon defining an internal inflatable chamber;
   a plurality of guide tubes being connected to said external surface of said first balloon;
   a first wire disposed in at least one of said guide tubes; and
   a second wire disposed in at least a second one of said guide tubes, each of said first wire and said second wire having means for being electrically connected to an MRI apparatus.

28. The magnetic resonance image receiving coil in accordance with claim 27, wherein said plurality of guide tubes include two guide tubes that are disposed at approximately 90° intervals with respect to each other.

29. The magnetic resonance image receiving coil in accordance with claim 27, wherein an elastic shaft is disposed within said first balloon.

30. The magnetic resonance image receiving coil in accordance with claim 28, wherein an elastic shaft is disposed within said first balloon.

31. The magnetic resonance image receiving coil in accordance with claim 27, wherein said first and second wires are coaxial cable.

32. The magnetic resonance image receiving coil in accordance with claim 31, wherein each of said first and second wires are connected to a tuning capacitor in a parallel circuit.

33. The magnetic resonance image receiving coil in accordance with claim 31, wherein each of said first and second wires are connected to a tuning capacitor in a parallel circuit.

* * * * *